United States Patent
Ranjan et al.

(10) Patent No.: US 6,660,696 B1
(45) Date of Patent: Dec. 9, 2003

(54) THERMALLY STABLE PHOSPHOROTHIONATES AS ANTIOXIDANT, ANTIWEAR, FRICTION REDUCING AND EXTREME PRESSURE LUBRICANT ADDITIVES FROM CASHEW NUT SHELL LIQUID

(75) Inventors: Rajeev Ranjan, Maharashtra (IN); Ajay Kumar Arora, Maharashtra (IN); Rakesh Sarin, Maharashtra (IN); Deepak Kumar Tuli, Maharashtra (IN); Ram Prakash Verma, Maharashtra (IN); Akhilesh Kumar Bhatnagar, Maharashtra (IN)

(73) Assignee: Indian Oil Corporation Limited, Maharashtra (IN)

(*) Notice: Subject to any disclaimer, the term of this patent is extended or adjusted under 35 U.S.C. 154(b) by 0 days.

(21) Appl. No.: 10/189,374

(22) Filed: Jun. 20, 2002

(30) Foreign Application Priority Data

May 24, 2002 (IN) .................... 459/MUM/2002

(51) Int. Cl.⁷ ............................................ C10M 137/10
(52) U.S. Cl. ........................... 508/433; 558/90; 558/92; 558/208; 252/400.21
(58) Field of Search ................ 508/136, 433; 558/90, 92, 208; 252/400.21

(56) References Cited

U.S. PATENT DOCUMENTS

| | | |
|---|---|---|
| 4,395,498 A | 7/1983 | Benham |
| 5,218,038 A | 6/1993 | Johnson et al. |
| 5,433,774 A | 7/1995 | Kapl et al. |
| 5,531,911 A * | 7/1996 | Adams et al. ............... 508/408 |
| 5,910,468 A | 6/1999 | Tuli et al. |
| 5,916,850 A | 6/1999 | Tuli et al. |
| 6,229,054 B1 * | 5/2001 | Dai et al. .................... 568/630 |
| 6,339,052 B1 | 1/2002 | Dohhen et al. |

* cited by examiner

Primary Examiner—Jacqueline V. Howard
(74) Attorney, Agent, or Firm—Sidley Austin Brown & Wood LLP

(57) ABSTRACT

Phosphorothionate derivatives derived from cashew nut shell liquid (CNSL) for use as an thermally stable antioxidant, antiwear, friction reducing and extreme pressure additive in a lubricant composition are synthesized by the steps of (a) partially hydrogenating distilled technical cashew nut shell liquid with palladium or nickel or platinum catalyst; to hydrogenate the olefinic chain; (b) reacting partially hydrogenated technical cashew nut shell liquid with phosphorus trihalide and sulphur, the reaction being carried out at a temperature ranging from 20 to 220° C. A lubricant containing a major proportion of a material selected from the group consisting of an oil of lubricating viscosity or a grease; and remainder an additive including CNSL phosphorothionate derivative, prepared by the foregoing process.

30 Claims, No Drawings

THERMALLY STABLE PHOSPHOROTHIONATES AS ANTIOXIDANT, ANTIWEAR, FRICTION REDUCING AND EXTREME PRESSURE LUBRICANT ADDITIVES FROM CASHEW NUT SHELL LIQUID

This invention relates to thermally Stable phosphorothionates from cashew nut shell liquid for use as thermally stable, antioxidant, antiwear and extreme pressure additives in a lubricant composition. The said additive for use in a lubricant controls wear on metal parts and enhances its load carrying properties.

BACKGROUND

Lubrication involves the process of friction reduction, accomplished by maintaining a film of a lubricant between two surfaces which are moving with respect to each other. The lubricant prevents contact of the moving surfaces, thus greatly lowering the coefficient of friction. Since lubricants for different uses operate under different conditions, numerous additives have been developed to establish or enhance various properties of lubricants. Representative types of additives which are used include viscosity improvers, detergents, dispersants, antioxidants, extreme pressure additives, corrosion inhibitors and others. Frequently, combinations of additives are required.

Of particular importance in many applications are antiwear agents, many of which function by a process of interaction with the surfaces, thereby providing a chemical film which prevents metal-to-metal contact under high load conditions. Wear inhibitors which are useful under extremely high load conditions are frequently called "extreme pressure agents". These extreme pressure agents are frequently selected from the following chemical types: zinc organodithiophosphates; sulfurized olefins, chlorinated waxes; amine salts of phosphate esters; phosphites; and others. Certain of these materials, however, must be used judiciously in certain applications due to their property of accelerating corrosion of metal parts, such as bearings. In addition, some applications require very low concentrations of certain elements, such as phosphorus, which restricts the utility of otherwise quite useful extreme pressure agents.

An exhaustive literature review was conducted to examine the types of chemistries in use as antiwear and EP additives. Example of antiwear and extreme pressure additives are: sulfur-and/or phosphorous-and/or halogen-containing compounds, such as sulfurized olefins and vegetable oils, zinc dialkyldithiophosphates, tritolyl phosphate, tricresyl phosphate, chlorinated paraffins, alkyl and aryl di- and trisulfides, amine salts of mono- and dialkyl phosphates, amine salts of methylphosphonic acid, diethanolaminomethyl tolyltriazole, di(2-ethylhexyl)-aminomethyltolyltriazole, derivatives of 2,5-dimercapto-1,3,4-thiadiazole, triphenylthiophosphate (triphenyl phosphorothioate), diphenylmonononylphenyl phosphorothioate, isobutylphenyl diphenyl phosphorothioate, derivatives of 2-mercaptobenzothiazole and ethoxycarbonyl 5-octyldithiocarbamate.

The object of the present invention is to provide for a thermally stable, antioxidant, antiwear and extreme pressure lubricant additive, derived from CNSL, a renewable and biodegradable product from vegetable sources and often available at very low price, which would amount to substantial overall reduction in the cost of quality, energy efficient lubricant/fuel formulations.

Another object of the present invention is to provide for a lubricant composition and more particularly, to lubricant compositions comprising oils of lubricating viscosity or greases thereof containing a minor thermally stable antioxidant, antiwear and extreme pressure additive derived from cashew nut shell liquid.

Cashew nut shell liquid (CNSL) occurs as a reddish brown viscous liquid in the soft honeycomb structure of the shell of cashewnut, a plantation product obtained from the cashew tree, Anacardium Occidentale L. Native to Brazil, the tree grows in the coastal areas of Asia & Africa. Cashewnut attached to cashew apple is grey colored, kidney shaped and 2.5–4 cm long. The shell is about 0.3 cm thick, having a soft leathery outer skin and a thin hard inner skin. Between these skins is the honeycomb structure containing the phenolic material popularly called CNSL. Inside the shell is the kernel wrapped in a thin brown skin, known as the testa.

The nut thus consists of the kernel (20–25%), the shell liquid (20–25%) and the testa (2%), the rest being the shell. CNSL, extracted with low boiling petroleum ether, contains about 90% anacardic acid and about 10% cardol. CNSL, on distillation, gives the pale yellow phenolic derivatives, which are a mixture of biodegradable unsaturated m-alkylphenols, including cardanol. Catalytic hydrogenation of these phenols gives a white waxy material, predominantly rich in tetrahydroanacardol.

CNSL and its derivatives have been known for producing high temperature phenolic resins and friction elements, as exemplified in U.S. Pat. Nos. 4,395,498 and 5,218,038. Friction lining production from CNSL is also reported in U.S. Pat. No. 5,433,774. Likewise, it is also known to form different types of friction materials, mainly for use in brake lining system of automobiles and coating resins from CNSL. However, the first application of CNSL in making lubricating oil additives was disclosed by us in U.S. Pat. Nos. 5,916,850 and 5,910,468.

Our U.S. Pat. No. 5,916,850 described development of multifunctional additives from cashew nut shell liquid or from saturated alkylphenols derived from cashew nut shell liquid. The patent relates to a process for preparing tri (alkylaryl) phosphorodithioate. The products of this invention were found to have better antifriction, extreme pressure and antiwear properties. In another U.S. Pat. No. 5,910,468, cashew nut shell liquid has been exploited for developing overbased calcium phenate detergents as additives for lubricant formulations. In another U.S. Pat. No. 6,339,052, additives derived from cashew nut shell liquid were exploited in lubricant compositions for internal combustion engines.

DETAILED DESCRIPTION OF THE INVENTION

To achieve the said objects, the present invention provides for CNSL phosphorothionates. It also provides for a process for the preparation of CNSL phosphorothionates for use as an thermally stable, antioxidant, antiwear and extreme pressure additive in a lubricant composition, comprising the steps of hydrogenating distilled technical cashew nut shell liquid (CNSL) with a catalyst as herein described to fully hydrogenate the olefinic chain and reacting said cashew nut shell liquid with phosphorus trihalides and sulphur, the reaction being carried out at a temperature ranging from 20 to 220° C.

The materials of the present invention are useful as additives for lubricants in which they can function primarily as thermally stable antiwear, antiscuff, and/or extreme pressure agents. They may be employed in a variety of lubricants based on diverse oils of lubricating viscosity, including natural and synthetic lubricating oils and mixtures thereof. These lubricants include crankcase lubricating oils for spark-ignited and compression-ignited internal combustion engines, including automobile and truck engines, two-cycle engines, aviation piston engines, marine and railroad diesel engines, and the like. They can also be used in gas engines, stationary power engines and turbines and the like. Automatic or manual transmission fluids, transaxle lubricants, gear lubricants, including open and enclosed gear lubricants, tractor lubricants, metal-working lubricants, hydraulic fluids and other lubricating oil and grease compositions can also benefit from the incorporation therein of the compositions of the present invention. They may also be used as wirerope, walking cam, way, rock drill, chain and conveyor belt, worm gear, bearing, and rail and flange lubricants.

The compounds of the invention can be incorporated into lubricating oils and power transmitting oils as an antiwear additive in an amount from between about 0.01 to 5 wt. %, preferably from between about 0.1 to 1.5 wt. %, most preferably from between about 0.2 to 1.0 wt. %. The oleaginous materials may be formulated to contain other additives such as viscosity modifiers, auxiliary antioxidants, friction modifiers, dispersants, antifoaming agents, auxiliary antiwear agents, pour point depressants, detergents, rust inhibitors and the like.

Compositions containing the above additives are typically blended into base oils in amounts sufficient to provide their normal attendant function. Representative examples of amounts in which these additives are conventionally to lubricating oils are as follows:

| Additive | Wt. % (broad) | Wt. % (preferred) |
|---|---|---|
| Viscosity Modifier | 0.01–12 | 0.01–4 |
| Corrosion Inhibitor | 0.01–5 | 0.01–1.5 |
| Oxidation Inhibitor | 0.01–5.0 | 0.01–1.5 |
| Pour Point Depressant | 0.01–5.0 | 0.01–1.5 |
| Dispersant | 0.1–20.0 | 0.1–8.0 |
| Anti-Foaming Agents | 0.01–3.0 | 0.01–0.15 |
| Anti-Wear Agents | 0.01–5.0 | 0.01–2.0 |
| Friction Modifiers | 0.01–5.0 | 0.01–2.5 |
| Detergents | 0.01–10.0 | 0.01–3.0 |
| Rust Inhibitors | 0.01–4.0 | 0.01–2.0 |
| Base Oil | Balance | Balance |

The additives can be incorporated into the lubricating oil in any convenient manner. Thus, they can be added directly to the oil by dispersing or dissolving same in the oil. Such blending can be performed at room temperature or at elevated temperatures. Alternatively, the additives may be first formed into concentrates, which are subsequently blended with the oil. The final formulations may typically contain from between about 2 wt. % to 20 wt. % of additives.

Suitable dispersants include hydrocarbyl succinimides, hydrocarbyl succinamides, mixed ester/amides of hydrocarbyl substituted succinic acid, hydroxyesters of hydrocarbyl-substituted succinic acid, amides of aromatic acids and Mannich condensation products of hydrocarbyl-substituted phenols, formaldehyde and polyamines. Mixtures of such dispersants can also be employed.

The preferred dispersant for use in combination with the CNSL phosphorothionate additives of the present invention are alkenyl succinimides. These acyclic hydrocarbyl substituted succinimides are formed with various amines, polyamines and amine derivatives, and are well known to those of ordinary skill in the art. An example of a particularly suitable dispersant is the polyisobutenyl succinimide reaction product of polyisobutylene succinic anhydride, wherein the polyisobutene moiety preferably has a number average molecular weight in the range from between about 500 to 5000, preferably from between about 800 to 2500 and an alkylene polyamine such as triethylene tetramine or tetraethylene pentamine or mixtures of polyamines containing 3 to 12 nitrogen atoms per molecule, known in the art as PAM. The use of alkenyl succinimides that have been treated with an inorganic acid of phosphorus (or an anhydride thereof) and a boronating agent are also suitable for use in combination with the compounds of the invention and are more compatible with elastomeric seals made from such substances as fluoroelastomers and silicon elastomers.

Suitable antioxidants for use in combination with the additives of the present invention include amine-type and phenolic antioxidants. Examples of amine-type antioxidants include phenyl alpha napthylamine, phenyl beta naphthalyamine and bis- alkylated diphenyl amines (e.g., p,p'-bis(alkylphenyl)-amines wherein the alkyl groups each contain from 8 to 12 carbon atoms). Phenolic antioxidants include sterically hindered phenols (e.g., 2,6-di-tert-butylphenol, 4-methyl-2,6-di-tert-butylphenol) and bis-phenols (e.g., 4,4"-methylenebis(2,6-di-tert-butylphenol). Phosphorous compounds, such as ZDDP, or phosphites are also commonly added to automatic transmission fluids (ATF) and passenger car motor oils (PCMO) as antioxidants. In addition to providing antiwear properties, the compounds of the present invention provide antioxidant credits to lubricating compositions, allowing for the formulation of lubricating compositions with a reduced amount, or no amount, of dedicated antioxidant additive.

Suitable friction modifiers are molecules having a polar head group and an oleophilic tail group. The polar head groups cause the molecule to be adsorbed onto the friction surface. These groups can be, but are not limited to, amines, mono and diethoxylated amines, carboxylic acids, amides, imides, alcohols, phenols, thiols, sulfonic acids, phosphites, phosphates, esters and combinations thereof. The oleophilic groups are typically alkyl groups, normally linear alkyl groups. These alkyl groups range in carbon number from between about $C_8$ to $C_{30}$, preferably from $C_{12}$ to $C_{20}$. They may be saturated or unsaturated, and may contain hetero atoms such as nitrogen or sulfur providing that the hetero atoms do not adversely affect the ability of the molecule to function as a friction modifier.

Examples of friction modifiers suitable for use with the antiwear additives of the invention include oleamide, tallow amine, diethoxylated tallow amine, N,N-bis(2-hydroxyethyl)-octadecyl amine, N,N-bis(2-hydroxyethyl)-stearyloxypropylamine, oleic acid, N,N-hydroxyethyl,N-(N', N'-bis(2-hydroxyethyl)ethylamine)-stearylamine and the diamide produced from isostearic acid and tetraethylene pentamine, molybdenum dithiocarbamates and molybdenum dithiophosphates.

Suitable compounds for use as viscosity modifiers are generally high molecular weight hydrocarbon polymers, including polyesters. Oil soluble viscosity modifying polymers generally have weight average molecular weights from about 10,000 to 1,000,000, preferably from about 20,000 to 500,000, as determined by gel permeation chromatography or light scattering methods.

Representative examples of suitable viscosity modifiers are polyisobutylene, copolymers of ethylene and propylene and higher alpha-olefins, polymethacrylates, polyalkylmethacrylates, methacrylate copolymers, copolymers of unsaturated dicarboxylic acid and vinyl compound, inter polymers of styrene and acrylic esters, and partially hydrogenated copolymers of styrene/isoprene, styrene/butadiene and isoprene/butadiene, as well as partially hydrogenated homopolymers of butadiene and isoprene and isoprene/divinylbenzene.

Lubricating oils and power transmission oils incorporating the antiwear additives of the invention may also contain rust inhibitors such as nonionic polyoxyalkylene polyols and esters thereof, polyoxyalkylene phenols, phenoxyacetic acids and anionic alkyl sulfonic acids, as well as corrosion inhibitors, such as thiadiazole polysulfides containing from between about 5 to 50 carbon atoms, their derivatives and polymers thereof; derivatives of 1,3,4-thiadiazoles; and thio and polythio sulfenamides of thiadiazoles. Such oils may also contain an antifoamant, including polyacrylate-type antifoamants, polysiloxane-type antifoamants and fluorosilicone-type antifoamants, and detergents, such as overbased and neutral calcium sulfonate, calcium phenate, magnesium sulfonate and magnesium phenate.

Generally speaking, the process of manufacturing the additives in accordance with this invention may be carried out as follows:

Specifically, cashew nut shell liquid is distilled at reduced pressure to yield a mixture of biodegradable olefinic phenols. The components of CNSL contain a phenolic hydroxyl group and an $C_{15}H_{31-n}$ unsaturated side chain, where n=0, 2,4 or 6. Such a mixture is converted to their saturated $C_{15}$ phenol derivatives by catalytic reduction in the presence of a palladium or platinum or nickel hydrogenation catalyst. The alkyl phenol is treated with phosphorus trihalides and sulphur in the presence of a solvent. After the completion of the reaction, the solvent is removed and product extracted with another organic solvent to yield the desired CNSL phosphorothionate derivatives.

Triaryl thiophosphates are known plasticizing and flame retardant agents for polymers. However, symmetrical triaryl thiophosphates e.g triphenyl phosphate, are crystalline solids. This detracts from their use as plasticizers as they have a tendency to crystallize and bloom to the surface of the plasticized composition. As solids, these compounds are difficult to process and handle. They also have a disagreeable $H_2S$ odor.

The composition of the invention can also be prepared by forming a mixture of cashew nut shell liquid and phenol or substituted phenol. This cardanol mixture is then reacted with a phosphorous trihalide, e.g chloride or bromide, in an amount sufficient to completely substitute to halide cites though more or less can be used. Generally 3.0–3.5 molecular equivalents (~5–15% excess) of the phenols as per molecular equivalent of phosphorous trihalide is used. The reaction is carried out by heating mixture of reactants to a temperature at which hydrogen halide is involved, i.e. between about 30° C. and about 200° C. If desired a nitrogen sparge and a catalyst such as a metal or metallic chloride catalyst can be employed. Any excess phenol can be stripped under vacuum. The triaryl phosphite/mixed triaryl phosphite product can then be reacted directly with sulphur to form the triaryl thiophosphate/ mixed triaryl thiophosphate final product. The reaction with the sulphur is generally carried out by heating the reactants with an amount of sulphur, preferably powdered sulphur, equimolar to the phosphite at temperature ranging from about 140° C. to about 250° C. for a sufficient time to accomplish the reaction depending on temp and reactants, e.g. for about 1–3 hours, to yield CNSL phosphorothionates.

The compounds of the invention can also be prepared by reacting thiophosphoryl chloride with the cardanol and mixed phenol blend. The sulfurization step can be avoided though the other steps apply. When using thiophosphoryl chloride it is again important to the operation of the invention that any distillation be prior to the base washing and mild drying.

The following examples illustrate the invention, but without intending to imply any limitation thereon.

EXAMPLE 1

Partial Hydrogenation of Distilled Technical Cashew Nut Shell Liquid (CNSL)

Distilled technical CNSL was charged to a Parr Reactor with about 1% of Nickel hydrogenation catalyst (containing 25% Nickel) or about 0.2% of Palladium on carbon (containing 10% Pd) or about 0.2% of Platinum on alumina. The reactor was charged with hydrogen at 200 Psi and at 130° C. for about 5 hours. The reaction was monitored by NMR & GC to check the reduction of olefinic chain, while controlling the conditions so as not to reduce the phenolic ring. On completion of the reaction, the catalyst was filtered out and saturated cardanol phenol was isolated.

EXAMPLE 2

Preparation of Tricardanol Phosphorothionate (I)

In a multinecked round bottom flask fitted with stirrer, thermometer pocket, $N_2$ inlet and condensor take 0.6 mole of cardanol. Raise temperature to 55° C. under $N_2$ atmosphere and add 0.172 mol of $PCl_3$ dropwise such that temperature of the reaction mixture does not exceed 70° C. Raise temperature to 150° C. and maintain for 2 h. Stop heating, cool the reaction mixture to room temperature, add toluene as the diluent. Wash the reaction mixture with 5% NaOH soln. and brine solution. Recover solvent to obtain triarylphosphite (yield 80%). To 0.1 mole of phosphite add 0.10 mole of elemental sulfur, raise temperature to 180° C. and maintain for 3 h to obtain compound I(yield 75%, viscous liquid). $^{31}P$ NMR spectra shows single peak at 52.97 ppm corresponding to pentavalent phosphorus. IR spectra shows stretch at 691.2 cm$^{-1}$ corresponding to P=S group. m/e=972 confirming formation of the product.

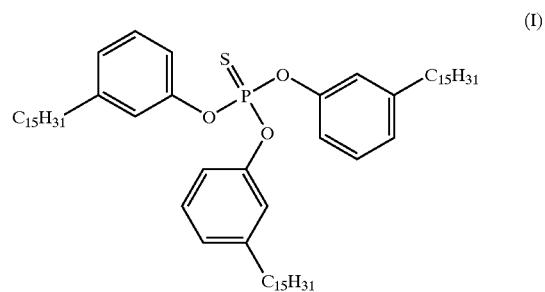

(I)

EXAMPLE 3

Preparation of Dicardanol Monophenyl Phosphorothionate (II, R=H)

In a similar set up as above take 0.4 mole of cardanol and 0.2 mol of phenol. Raise temperature to 55° C. under $N_2$ atmosphere and add 0.172 mol of $PCl_3$ dropwise such that temperature of the reaction mixture does not exceed 70° C.

Raise temperature to 150° C. and maintain for 3 h. Stop heating, cool the reaction mixture to room temperature, add methyl ethyl ketone so as to thin the compound Wash the reaction mixture with 5% NaOH soln. and brine solution. Recover solvent to obtain the corresponding phosphite (yield 85%). To 0.13 mole of phosphite add 0.13 mole of elemental sulfur, raise temperature to 180° C. and maintain for 3 h to obtain compound II (yield 75%, viscous liquid).

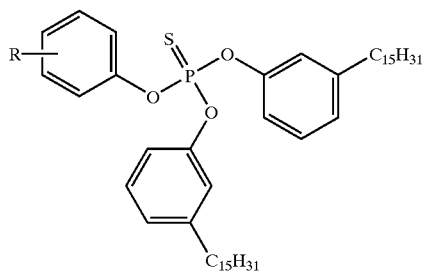

(II)

$^{31}$P NMR spectra shows single peak at 53.5 ppm, IR spectra shows stretch at 694.1 cm$^{-1}$ corresponding to P=S group and m/e=764 confirming formation of the product.

EXAMPLE 4

Preparation of Monocardanoldiphenylphosphorothionate (III, R$^1$=R$^2$=H)

Take 0.1 mole of cardanol and 0.2 mol of phenol in a multinecked round bottom flask fitted with stirrer, thermometer pocket, N$_2$ inlet and condensor. Raise temperature to 55° C. under N$_2$ atmosphere and add 0.086 mol of PCl$_3$ dropwise. After completion of addition raise temperature of the reaction mixture to 150° C. and maintain for 2 h. Stop heating, cool the reaction mixture to room temperature, add toluene as a diluent. Wash the reaction mixture with 10% NaOH soln. and water. Recover solvent to obtain the phosphite (yield 78%). To 0.06 mole of phosphite add 0.06 mole of elemental sulfur, raise temperature to 180° C. and maintain for 4 h to obtain compound III (yield 80%, viscous liquid).

$^{31}$P NMR spectra shows single peak at 52.8 ppm corresponding to pentavalent phosphorus. IR spectra shows stretch at 691.0 cm$^{-1}$ corresponding to P=S group. m/e 552 confirming formation of the product.

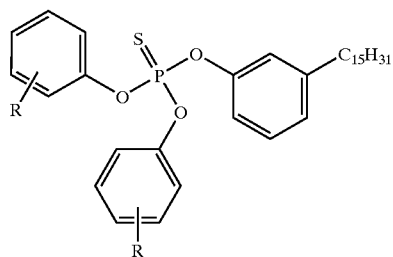

(III)

EXAMPLE 5

Preparation of Dicardanol mono(m) Cresolphosphorothionate (II, R=m-CH$_3$)

In a similar set up as above take 0.4 mole of cardanol and 0.2 mol of m-cresol. Raise temperature to 55° C. under N$_2$ atmosphere and add 0.172 mol of PCl$_3$ dropwise such that temperature of the reaction mixture does not exceed 70° C. Raise temperature to 150° C. and maintain for 3 h. Stop heating, cool the reaction mixture to room temperature, add methyl ethyl ketone so as to thin the compound Wash the reaction mixture with 5% NaOH soln. and brine solution. Recover solvent to obtain the corresponding phosphite (yield 83%). To 0.12 mole of phosphite add 0.12 mole of elemental sulfur, raise temperature to 180° C. and maintain for 4 h to obtain compound II (yield 80%, viscous liquid).

$^{31}$P NMR spectra shows single peak at 54.1 ppm, IR spectra shows stretch at 690.5 cm$^{-1}$ corresponding to P=S group and m/e=776 confirming formation of the product.

EXAMPLE 6

Preparation of Monocardanol di(m) Cresolphosphorothionate (III, R$^1$=R$^2$=m-CH$_3$)

Take 0.1 mole of cardanol, and 0.2 mol of m-cresol in a multinecked round bottom flask fitted with stirrer, thermometer pocket, N$_2$ inlet and condensor. Raise temperature to 55° C. under N$_2$ atmosphere and add 0.0.086 mol of PCl$_3$ dropwise. After completion of addition raise temperature of the reaction mixture to 150° C. and maintain for 2 h. Stop heating, cool the reaction mixture to room temperature, add toluene as a diluent. Wash the reaction mixture with 10% NaOH soln. and water. Recover solvent to obtain the phosphite (yield 88%). To 0.06 mole of phosphite add 0.06 mole of elemental sulfur, raise temperature to 180° C. and maintain for 4 h to obtain compound III (yield 80%, viscous liquid). $^{31}$P NMR spectra shows single peak at 53.8 ppm corresponding to pentavalent phosphorus. IR spectra shows stretch at 691.0 cm$^{-1}$ corresponding to P=S group. m/e=580 confirming formation of the product.

EXAMPLE 7

Preparation of Tricardanol Phosphorothionate (I)

In a multinecked round bottom flask fitted with stirrer, thermometer pocket, N$_2$ inlet and condenser take 0.3 mole of cardanol. Raise temperature to 55° C. under N$_2$ atmosphere and add 0.086 mol of PCl$_3$ dropwise such that temperature of the reaction mixture does not exceed 70° C. Raise temperature to 150° C. and maintain for 2 h. To the reaction mixture add 0.08 mole of elemental sulfur, raise temperature to 180° C. and maintain for 3.5 h Stop heating, cool the reaction mixture to room temperature, add methyl ethyl ketone as the diluent. Wash the reaction mixture with 5% NaOH soln. and brine solution. Dry the solvent over anhyd. sodium sulfate Recover it to obtain compound I (yield 85%) $^{31}$P NMR spectra shows single peak at 52.8 ppm corresponding to pentavalent phosphorus. IR spectra shows stretch at 691.9 cm$^{-1}$ corresponding to P=S group, m/e =971 confirming formation of 1.

EXAMPLE 8

Preparation of Dicardanol Monophenyl Phosphorothionate (II, R=H)

In a setup as for example 2, take 0.2 mole of cardanol and 0.1 mole of phenol. Raise temperature to 55° C. under N$_2$ atmosphere and add 0.086 mol of PCl$_3$ dropwise. After completion of addition raise temperature of the reaction mixture to 150° C. and maintain for 2 h. To the reaction mixture add 0.09 mole of elemental sulfur raise temperature to 180° C. and maintain for 3 h Stop heating, cool the reaction mixture to room temperature, add methyl ethyl ketone as the diluent. Wash the reaction mixture with 5% NaOH soln. and brine solution. Dry the solvent over anhyd. sodium sulfate and recover it to obtain compound II (yield 80%) $^{31}$P NMR spectra shows single peak at 53.5 ppm corresponding to pentavalent phosphorus. IR spectra shows stretch at 694.5 cm$^{-1}$ corresponding to P=S group, m/e=764.

EXAMPLE 9

Preparation of Cardanol Diphenyl Phosphorothionate (III, R$^1$=R$^2$=H)

In a setup as for example 2, take 0.1 mole of cardanol and 0.2 mole of phenol. Raise temperature to 55° C. under N$_2$ atmosphere and add 0.086 mol of PCl$_3$ dropwise such that temperature of the reaction mixture does not exceed 70° C. Raise temperature to 150° C. and maintain for 1 h. To the reaction mixture add 0.08 mole of elemental sulfur, raise temperature to 180° C. and maintain for 2 h Stop heating, cool the reaction mixture to room temperature, add toluene as the diluent. Wash the reaction mixture with 5% NaOH soln. and brine solution. Dry the solvent over anhyd. sodium sulfate Recover it to obtain compound III (yield 85%) $^{31}$P NMR spectra shows single peak at 52.8 ppm corresponding to pentavalent phosphorus. IR spectra shows stretch at 691.

EXAMPLE 10

Preparation of Dicardanol Mono(m) Cresolphosphorothionate (II, R=m-CH$_3$)

In a setup as for example 2, take 0.2 mole of cardanol and 0.1 mole of m-cresol. Raise temperature to 55° C. under N$_2$ atmosphere and add 0.086 mol of PCl$_3$ dropwise. After completion of addition raise temperature of the reaction mixture to 150° C. and maintain for 2 h. To the reaction mixture add 0.09 mole of elemental sulfur, raise temperature to 180° C. and maintain for 3 h Stop heating, cool the reaction mixture to room temperature, add methyl ethyl ketone as the diluent. Wash the reaction mixture with 5% NaOH soln. and brine solution. Dry the solvent over anhyd. sodium sulfate and recover it to obtain compound II (yield 85%) $^{31}$P NMR spectra shows single peak at 54.0 ppm corresponding to pentavalent phosphorus. IR spectra shows stretch at 690.5 cm$^{-1}$ corresponding to P=S group, m/e=776.

EXAMPLE 11

Preparation of Cardanol di(m)Cresol Phosphorothionate (III, R$^1$=R$^2$=m-CH$_3$)

Take 0.1 mole of cardanol and 0.2 mole of m-cresol in a multinecked round bottom flask fitted with stirrer, thermometer pocket, N$_2$ inlet. Add 0.086 mol of PCl$_3$ dropwise such that temperature of the reaction mixture does not exceed 70° C. Raise temperature to 150° C. and maintain for 2 h. To the reaction mixture add 0.08 mole of elemental sulfur, raise temperature to 180° C. and maintain for 2 h Stop heating, cool the reaction mixture to room temperature, add toluene as solvent. Wash the reaction mixture with 10% NaOH soln. and brine solution. Dry the solvent over anhyd. sodium sulfate Recover it to obtain compound III (yield 80%) $^{31}$P NMR spectra shows single peak at 52.0 ppm corresponding to pentavalent phosphorus. IR spectra shows stretch at 685.9 cm$^{-1}$ corresponding to P=S group, m/e=580 confirming formation of desired product.

EXAMPLE 12

Preparation of Tricardanol Phosphorothionate (I)

Take 0.6 mole of phenol in a multinecked round bottom flask fitted with stirrer, thermometer pocket, N$_2$ inlet and condenser. Under N$_2$ atmosphere add 0.180 mol of thiophosphorylchloride dropwise such that temperature of the reaction mixture does not exceed 55° C. Raise temperature to 150° C. maintain for 2 h. and then raise temperature to 180° C. and maintain for 3 h. Stop heating, cool the reaction mixture to room temperature, add toluene as the diluent. Wash the reaction mixture with 5% NaOH soln. and brine solution. Dry the solvent over anhyd. sodium sulfate. Recover it to obtain compound I (yield 85%). $^{31}$P NMR spectra shows single peak at 53.0 ppm corresponding to pentavalent phosphorus. IR spectra shows stretch at 691.6 cm$^{-1}$ corresponding to P=S group, m/e =971 confirming formation of the product.

EXAMPLE 13

Preparation of Dicardanol Monophenyl Phosphorothionate (II, R=H)

In a multinecked round bottom flask fitted with stirrer, thermometer pocket, N$_2$ inlet and condenser take 0.4 mole of cardanol and 0.2 mole of phenol. Under N$_2$ atmosphere add 0.180 mol of thiophosphoryl chloride dropwise Raise temperature to 150° C. maintain for 2 h. and then raise temperature to 180° C. and maintain for 3 h. Stop heating, cool the reaction mixture to room temperature, add toluene as the diluent. Wash the reaction mixture with 5% NaOH soln. and brine solution. Dry the solvent over anhyd. sodium sulfate and recover it to obtain compound II (yield 80%) $^{31}$P NMR spectra shows single peak at 53.4 ppm IR spectra shows stretch at 693.0 cm$^{-1}$ corresponding to P=S group, and m/e=764.

EXAMPLE 14

Preparation of Monocardanol Diphenyl Phosphorothionate (III, R$^1$=R$^2$=H)

Take 0.1 mole of cardanol and 0.2 mole of phenol in a multinecked round bottom flask fitted with stirrer, thermometer pocket, N$_2$ inlet and condenser. Under N$_2$ atmosphere add 0.086 mol of thiophosphorylchloride dropwise such that temperature of the reaction mixture does not exceed 55° C. Raise temperature to 150° C. maintain for 2 h. and then raise temperature to 180° C. and maintain for 3 h. Stop heating, cool the reaction mixture to room temperature, add toluene as the diluent. Wash the reaction mixture with 5% NaOH soln. and brine solution. Dry the solvent over anhyd. sodium sulfate Recover it to obtain compound III (yield 80%) $^{31}$P NMR spectra shows single peak at 53.0 ppm corresponding to pentavalent phosphorus. IR spectra shows stretch at 691.5 cm$^{-1}$ corresponding to P=S group, m/e=552 confirming formation of the product.

EXAMPLE 15

Preparation of Dicardanol Mono(m)cresol Phosphorothionate (II, R=m-CH$_3$)

In a multinecked round bottom flask fitted with stirrer, thermometer pocket, N$_2$ inlet and condenser take 0.4 mole of cardanol and 0.2 mole of m-cresol. Under N$_2$ atmosphere add 0.180 mol of thiophosphorylchloride dropwise Raise temperature to 150° C., maintain for 2 h. and then raise temperature to 180° C. and maintain for 4 h. Stop heating, cool the reaction mixture to room temperature, add toluene as the diluent. Wash the reaction mixture with 5% NaOH soln. and brine solution. Dry the solvent over anhyd. sodium sulfate and recover it to obtain compound II (yield 85%) $^{31}$P NMR spectra shows single peak at 53.0 ppm IR spectra shows stretch at 690.5 cm$^{-1}$ corresponding to P=S group, and m/e=776.

EXAMPLE 16

Preparation of Monocardanol di(m)-Cresolphosphorothionate (III, $R^1=R^2$=m-CH$_3$)

Take 0.1 mole of cardanol and 0.2 mole of m-cresol in a multinecked round bottom flask fitted with stirrer, thermometer pocket, N$_2$ inlet and condenser. Under N$_2$ atmosphere add 0.086 mol of thiophosphorylchloride dropwise such that temperature of the reaction mixture does not exceed 55° C. Raise temperature to 150° C. maintain for 2 h. and then raise temperature to 180° C. and maintain for 3 h. Stop heating, cool the reaction mixture to room temperature, add methyl ethyl ketone as the diluent. Wash the reaction mixture with 5% NaOH soln. and brine solution. Dry the solvent over anhyd. sodium sulfate Recover it to obtain compound III (yield 80%) $^{31}$P NMR spectra shows single peak at 53.2 ppm corresponding to pentavalent phosphorus. IR spectra shows stretch at 691.5 cm$^{-1}$ corresponding to P=S group, m/e= 580 confirming formation of the product.

EXAMPLE 17

Preparation of Cardanol m-Cresol p-Nonylphenol Phosphorothionate (III, $R^1$=m-CH3 and $R^2$=p-C9H19)

In a setup as for example 2, take 0.1 mole of cardanol, 0.1 mole of m-cresol and 0.1 mole of 0.1 mole of p-nonyl phenol. Raise temperature to 55° C. under N$_2$ atmosphere and add 0.09 mol of PCl$_3$ dropwise such that temperature of the reaction mixture does not exceed 70° C. Raise temperature to 150° C. and maintain for 1 h. To the reaction mixture add 0.08 mole of elemental sulfur, raise temperature to 180° C. and maintain for 2 h. Stop heating, cool the reaction mixture to room temperature and add toluene as the diluent. Wash the reaction mixture with 5% NaOH soln. and brine solution. Dry the solvent over anhyd. sodium sulfate and purified by column chromatography to obtain compound III $R^1$=m-CH3 and $R^2$=p-C9H19) (yield 85%). $^{31}$P NMR spectra shows single peak at 53.1 ppm corresponding to pentavalent phosphorus. IR spectra shows stretch at 691 cm$^{-1}$ for P=S functionality and m/e=692 confirming formation of the desired product.

Performance Evaluation of Products

Cost and time prohibit real-life testing of stabilizer systems, therefore laboratory tests have been developed to simulate conditions under which degradation occurs. Thermal gravimetric analysis (TGA) is a sensitive technique used to follow the weight change of a sample as a function of temperature, thereby providing information about the thermal stability, volatility and decomposition temperature of the additive studied. The test simulates conditions which the additive would experience during operation and usage.

As shown in Table I, TGA scans were used to measure the thermal stability of a series of phosphorothionates shown previously by formulae (I), (II) and (III). The percentage weight loss of the starting phosphorothionate was determined as a function of temperature.

TABLE 1

Thermal stability of Triarylphosphorothionates by Thermal Gravimetric Analysis (TGA)

| % Weight loss | Additive (I) Temp (° C.) | Additive (II, R = H) Temp (° C.) | Additive (III, $R^1$ = $R^2$ = H) Temp (° C.) | Additive (III, $R^1$ = $R^2$ = m-CH$_3$) Temp (° C.) | Additive (III, $R^1$ = p-C$_9$H$_{19}$, $R^2$ = m-CH$_3$) Temp (° C.) | Ref. Additive (Triphenyl Phosphorothionate) (° C.) |
|---|---|---|---|---|---|---|
| 5 | 250 | 250 | 250 | 240 | 240 | 210 |
| 10 | 320 | 290 | 280 | 280 | 250 | 230 |
| 15 | 380 | 320 | 310 | 310 | 280 | 235 |
| 20 | 430 | 350 | 330 | 340 | 330 | 240 |
| 25 | 440 | 380 | 350 | 360 | 340 | 250 |
| 30 | 450 | 400 | 370 | 370 | 350 | 250 |
| 35 | 455 | 420 | 390 | 390 | 380 | 255 |
| 40 | 460 | 430 | 400 | 410 | 390 | 260 |
| 45 | 465 | 435 | 410 | 420 | 405 | 270 |
| 50 | 465 | 440 | 415 | 430 | 410 | 270 |
| 55 | 470 | 450 | 425 | 440 | 420 | 275 |
| 60 | 475 | 455 | 430 | 450 | 430 | 275 |
| 65 | 475 | 460 | 440 | 460 | 435 | 280 |
| 70 | 480 | 460 | 445 | 465 | 420 | 280 |
| 75 | 485 | 470 | 450 | 470 | 440 | 285 |
| 80 | 490 | 475 | 460 | 480 | 450 | 285 |
| 85 | 495 | 480 | 470 | 485 | 460 | 290 |
| 90 | 500 | 490 | 480 | 500 | 470 | 295 |
| 95 | 510 | 500 | 490 | 510 | 500 | 300 |
| 98 | 730 | 730 | 730 | 740 | 740 | 310 |

As shown in Table-I, monocardanol diphenyl phosphorothionates are more thermally stable than triphenyl phosphorothionates. With the addition of second and third CNSL phenol, the thermal stability further enhances. Tricardanol phosphorothionates gets fully decomposed at 730° C., vis-à-vis 310° C. in the case of triphenylphosphorothionates.

The synthesised CNSL phosphorothionate derivatives were evaluated in a solvent refined, highly paraffinic, 150 neutral grade, mineral base oil having a kinematic viscosity of 28.8 at 40° C. and 5.0 cSt at 100° C., for their antiwear and load carrying properties. The results of these tests are given in Table 2.

A four ball machine was used for studying antiwear properties, involving measurement of wear scar on the ball at 196N load, 55.degree. C. temperature and 1800 rpm for one hour. In general, triarylphosphorothionates reduced wear scar over unformulated base oil, by 20–60% at 0.5–1.0% dosage (Table-2).

Extreme pressure properties were determined by measuring the weld load, in duplicate, on a four ball machine according to ASTM D-2783 test method, while increasing the load in stages of 981N, 1099N, 1236N, 1570N, 1766N, 1962N and 2206N. Synthesised triarylphosphorothionates showed an increase in weld load from 25–50% at additive dosage of 0.5–2.0% (Table-1).

Antioxidant performance of the blends was determined by differential scanning calorimetry (DSC), adopting temperature range of 100–350.degree. C., heating rate of 10.degree. C. per minute and oxygen flow rate of 60–80 ml/minute. The temperature at the onset of oxidation was taken as the criterion for assessment of antioxidant performance. In general, claimed triarylphosphorothionates increased the temperature of the onset of oxidation by 65–95° C., w.r.t. unformulated base oil (Table-2).

Antifriction properties were measured by an oscillating friction and wear test apparatus, under the point contact conditions. The minimum stabilised value of the coefficient of the friction, recorded during the continuous run, was taken as a criterion for friction. Synthesised triarylphosphorothionates, at 0.5–1.0% level, reduced coefficient of friction by 35–55%, as compared to base oil (Table-2).

The above data clearly demonstrates that additive amounts of the triarylphosphorothionates, derived from CNSL, in premium quality automotive and industrial lubricants significantly enhance the lubricant's energy efficiency, antiwear, antioxidant and extreme pressure properties. The unique additives described in this patent application are useful at low concentrations, are non-metallic and do not contain any potentially corrosive sulfur. These salts can be readily prepared in a one pot process. Furthermore, development and use of these multifunctional lubricant/fuel additives, derived from CNSL, a renewable and biodegradable product from vegetable sources and often available at very low price, would amount to substantial overall reduction in the cost of quality, energy efficient lubricant/fuel formulations.

TABLE 2

Performance evaluation of CNSL Phosphorothionates

| Compound | Dosage (% wt) | Weld load | Wear Scar Dia. @ 20 kg | Onset Oxid. Temp (° C.) | Coefficient of Friction |
|---|---|---|---|---|---|
| ADDITIVE I | 0.5 | 140 | 0.60 | 271 | 0.105 |
| ADDITIVE I | 1.0 | 160 | 0.80 | 275 | 0.10 |
| ADDITIVE II (R = H) | 0.5 | 140 | 0.70 | 245 | 0.11 |
| ADDITIVE II (R = H) | 1.0 | 160 | 0.70 | 264 | 0.105 |
| ADDITIVE III ($R^1 = R^2 = H$) | 0.5 | 126 | 1.0 | 261 | 0.11 |
| ADDITIVE III ($R^1 = R^2 = H$) | 1.0 | 160 | 0.50 | 266 | 0.105 |
| Additive (III, $R^1 = R^2 = $ m-$CH_3$) | 0.5 | 149 | 0.70 | 253 | 0.110 |
| Additive (III, $R^1 = R^2 = $ m-$CH_3$) | 1.0 | 160 | 0.55 | 267 | 0.105 |
| Additive (III, $R^1 = $ p-$C_9H_{19}$, $R^2 = $ m-$CH_3$) | 0.5 | 140 | 0.65 | 271 | 0.105 |
| Additive (III, $R^1 = $ p-$C_9H_{19}$, $R^2 = $ m-$CH_3$) | 1.0 | 160 | 0.50 | 289 | 0.10 |
| Triphenyl Phosphorothionate | 0.5 | 126 | 0.60 | 191 | 0.115 |
| Triphenyl Phosphorothionate | 1.0 | 140 | 0.40 | 190 | 0.11 |
| Base oil | | 126 | 0.95 | 180 | scuffed |

The above data clearly demonstrates that additive amounts of CNSL phosphorothionates, in premium quality automotive and industrial lubricants significantly control the wear and oxidation. The unique additives described in this patent application are useful at low concentrations, are non-metallic and do not contain any potentially corrosive sulfur. These salts can be readily prepared in a one pot process. Furthermore, development and use of these antiwear and antioxidant lubricant/fuel additives, derived from CNSL, a renewable and biodegradable product from vegetable sources and often available at very low price, would amount to substantial overall reduction in the cost of quality, energy efficient lubricant/fuel formulations.

We claim:

1. A cashew nut shell liquid phosphorothionate derivative of formula:

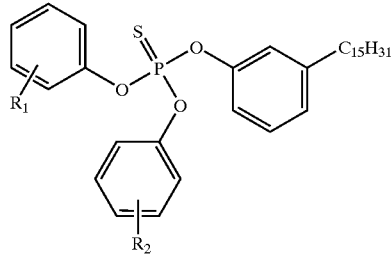

wherein $R_1$ and $R_2$ are H or alkyl or cycloalkyl or aryl at ortho, meta or para positions, with both $R_1$ and $R_2$ could be same or different, and one of the aryl moiety is derived from cashew nut shell liquid.

2. A cashew nut shell liquid phosphorothionate derivative as claimed in claim 1 wherein $R_2$ is $C_{15}H_{31}$ and $R_1$ is H or alkyl or cycloalkyl or aryl at ortho, meta or para positions of formula

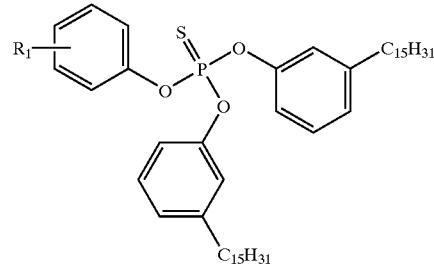

3. A cashew nut shell liquid phosphorothionate derivative as claimed in claim 1 wherein $R_1=R_2$ is $C_{15}H_{31}$ and the compound is tricardanol phosphorothionate, i.e., O,O'O"-tris(3-pentadecylphenyl)phosphorothioate, of formula

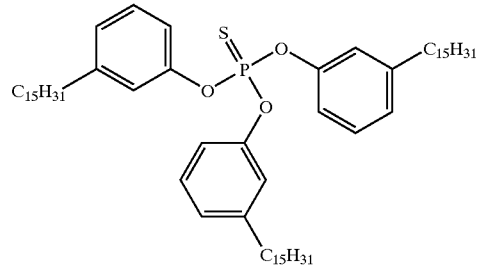

4. A cashew nut shell liquid phosphorothionate derivative as claimed in claim 1 wherein $R_2$ is m-$C_{15}H_{31}$; $R_1$ is H and the compound is dicardanol monophenyl phosphorothionate, i.e., O,O'-bis(3-pentadecylphenyl) O"-phenylphosphorothioate.

5. A cashew nut shell liquid phosphorothionate derivative as claimed in claim 1 wherein $R_1=R_2$ is H and the compound is monocardanoldiphenylphosphorothionate, i.e., O,O'-bis(phenyl)O"-3-pentadecylphenylphosphorothioate.

6. A cashew nut shell liquid phosphorothionate derivative as claimed in claim 1 wherein $R_1=R_2$ is m-$CH_3$ and the compound is monocardanoldi(m)cresol phosphorothionate, i.e., O,O'-bis(3-methylphenyl)O"-3-pentadecylphenylphosphorothioate.

7. A cashew nut shell liquid phosphorothionate derivative as claimed in claim 1 wherein $R_2$=p-$C_9H_{19}$; $R_1$=m-$CH_3$ and the compound is cardanol p-nonylphenyl.

8. A mixture of phosphorothionate derivatives as claimed in claim 1.

9. A process for the preparation of cashew nut shell liquid phosphorothionate derivatives, as claimed in claim 1, for use as an additive in a lubricant composition comprising the steps of:
(a) partially hydrogenating distilled technical cashew nut shell liquid with a catalyst to fully hydrogenate the olefinic chain;
(b) reacting said partially saturated cashew nut shell liquid with phosphorus trihalide and sulphur, the reaction being carried out at a temperature ranging from 20 to 140° C.

10. The process as claimed in claim 9 wherein said catalyst is selected from the group consisting of palladium, platinum or nickel.

11. The process as claimed in claim 9, wherein the phosphorus trihalide is selected from the group consisting of phosphorous trichloride, phosphorus tribromide, and phosphorus tri-iodide.

12. The process as claimed in claim 9, wherein the reaction is carried out in the presence of a solvent.

13. A process for the preparation of cashew nut shell liquid phosphorothionate derivatives, as claimed in claim 1, for use as an additive in a lubricant composition comprising the steps of:
reacting a cardanol mixture with a phosphorus trihalide in a predetermined amount sufficient to completely substitute halide sites at a temperature between about 30° C. to about 200° C. and
sulfurization of the reaction product at a temperature ranging between about 140° C. to about 250° C.

14. A process as claimed in claim 13 wherein the cardanol mixture comprises a mixture of cashew nut shell liquid and a phenol or substituted phenol.

15. A process as claimed in claim 14 wherein about 3.0 to 3.5 molecular equivalents of phenols as per molecular equivalent of phosphorus trihalide is used.

16. A lubricant composition comprising:
a major proportion of a material selected from the group consisting of an oil of lubricating viscosity and a grease and remainder an additive comprising cashew nut shell liquid phosphorothionates of claim 1.

17. The lubricant composition as claimed in claim 16, wherein the additive is present in an amount ranging from about 0.01 to about 5 wt %.

18. The lubricant composition as claimed in claim 16, wherein, the oil of lubricating viscosity is selected from the group consisting of a mineral oil, a synthetic oil, and mixtures thereof.

19. The lubricant composition as claimed in claim 18 wherein said synthetic oil is selected from the group consisting of polypropylene glycol, trimethylol propane esters, neopentyl esters, pentaerythritol esters, polyethylene glycol, di(2-ethylhexyl) adipate, fluorocarbons, siloxanes, phenoxy phenyl ethers and poly alphaolefins.

20. The lubricant as claimed in claim 16, wherein said material is a grease selected from the group consisting of a lithium grease, a calcium grease, a sodium grease, a clay, and a titanium grease.

21. The lubricant composition as claimed in claim 16 further comprising other additives selected from the group consisting of viscosity modifiers, auxiliary antioxidants, friction modifiers, dispersants, antifoaming agents, auxiliary antiwear agents, pour point depressants, detergents, and rust inhibitors.

22. The lubricant composition as claimed in claim 21 wherein said dispersants are selected from the group consisting of hydrocarbyl succinimides, hydrocarbyl succinamides, mixed ester/amides of hydrocarbyl substituted succinic acid, hydroxyesters of hydrocarbyl-substituted succinic acid, amides of aromatic acids and Mannich condensation products of hydrocarbyl-substituted phenols, formaldehyde and polyamines or mixtures thereof.

23. The lubricant composition as claimed in claim 21 wherein said antioxidants include amine-type and phenolic antioxidants.

24. The lubricant composition as claimed in claim 23 wherein said amine-type antioxidants are selected from the group consisting of phenyl alpha napthylamine, phenyl beta naphthylamine, bis-alkylated diphenyl amines, sterically hindered phenols, bis-phenols, phosphorus compounds and phosphites.

25. The lubricant composition as claimed in claim 21 wherein said friction modifiers suitable for use with the antiwear additives of the invention are selected from the group consisting of oleamide, tallow amine, diethoxylated tallow amine, N,N-bis(2-hydroxyethyl)-octadecyl amine, N,N-bis(2-hydroxyethyl)-stearyloxypropylamine, oleic acid, N,N-hydroxyethyl, N-(N',N'-bis(2-hydroxyethyl) ethylamine)-stearylamine and the diamide produced from isostearic acid and tetraethylene pentamine, molybdenum dithiocarbamates and molybdenum dithiophosphates.

26. The lubricant composition as claimed in claim 21 wherein said compounds for use as viscosity modifiers are generally high molecular weight hydrocarbon polymers, including polyesters.

27. The lubricant composition as claimed in claim 26 wherein said viscosity modifiers are selected from the group consisting of polyisobutylene, copolymers of ethylene, propylene and higher alpha-olefins, polymethacrylates, polyalkylmethacrylates, methacrylate copolymers, copolymers of unsaturated dicarboxylic acid and vinyl compounds, inter polymers of styrene and acrylic esters, partially hydrogenated copolymers of styrene/isoprene, styrene/butadiene and isoprene/butadiene, partially hydrogenated homopolymers of butadiene and isoprene, and isoprene/divinylbenzene.

28. A cashew nut shell liquid phosphorothionate derivative as claimed in claim 7 wherein said cardanol p-nonylphenyl is m-cresyl phosphorothionate (0-3-methylphenyl, 0'-4-nonylphenyl)"-0-3-pentadecylphenylphosphorothioate).

29. The lubricant composition as claimed in claim 16, wherein the additive is present in an amount ranging from about 0.03 to about 5 wt %.

30. The lubricant composition as claimed in claim 24 wherein said amine-type antioxidants is a p,p'bis (alkylphenyl)-amine wherein the alkyl groups each contain from 8 to 12 atoms.

* * * * *